United States Patent [19]

Yamauchi et al.

[11] Patent Number: 5,080,775
[45] Date of Patent: Jan. 14, 1992

[54] GAS DETECTOR

[75] Inventors: Shiro Yamauchi; Takahiko Inuzuka; Shoji Tada, all of Amagasaki, Japan

[73] Assignee: Mitsubishi Denki Kabushiki Kaisha, Tokyo, Japan

[21] Appl. No.: 652,672

[22] Filed: Feb. 8, 1991

[30] Foreign Application Priority Data

Apr. 25, 1990 [JP] Japan ................. 2-107479

[51] Int. Cl.5 ......................................... G01N 27/26
[52] U.S. Cl. .................................. 204/424; 204/421; 204/425; 204/426
[58] Field of Search ............... 204/421, 424, 425, 426

[56] References Cited

U.S. PATENT DOCUMENTS

| 3,764,269 | 12/1971 | Oldham et al. | 204/421 |
| 4,188,266 | 2/1980 | Forman | 204/421 |
| 4,298,573 | 11/1981 | Fujishiro | 204/425 |
| 4,306,957 | 12/1981 | Ishitani et al. | 204/426 |
| 4,388,155 | 6/1983 | Chamberland et al. | 204/426 |
| 4,487,680 | 12/1984 | Logothetis et al. | 204/425 |
| 4,505,805 | 3/1985 | Mase et al. | 204/425 |

Primary Examiner—John Niebling
Assistant Examiner—Bruce F. Bell
Attorney, Agent, or Firm—Oblon, Spivak, McClelland, Maier & Neustadt

[57] ABSTRACT

A gas detector, which has a memory function for detected data, such as the quantity of decomposed $SF_6$ gas, is for always watching whether electric discharging in the gas-insulated substation occurs or not, and comprises the laminated layers having a detecting electrode, a first conductive solid electrolyte, a polarization electrode, a second conductive solid electrolyte and a reference electrode.

6 Claims, 4 Drawing Sheets

GAS DETECTOR

FIELD OF THE INVENTION AND RELATED ART STATEMENT

1. Field of the Invention

The present invention relates to a gas detector for detecting undesirable decomposed $SF_6$ gas generated by electric discharging in a gas-insulated substation (GIS).

2. Description of the Related Art

Conventional gas detector which makes use of the characteristics of solid electrolyte has been disclosed, for instance, in the Japanese published unexamined patent application No. Sho 61-200456 (Tokkai sho 61-200456) which was filed by the same assignee. The gas detector has a solid electrolyte sensor device for detecting electric discharging in the gas-insulated substation (GIS) where $SF_6$ gas is filled. The gas detector which is of a dry method type produces an electric signal for indicating the existence of electric discharging.

The above-mentioned conventional gas detector has the structure shown in FIG. 4, which is a sectional view with schematic circuit diagram.

As shown in FIG. 4, the gas detector has a supplying electrode 1 which is made of platinum [Pt] wires formed in mesh to supply a detecting electrode 2 with electricity. The detecting electrode 2 is made of a deposition layer of metal copper [Cu] a quantity of which is already known. The copper layer as the detecting electrode 2 is formed on a surface of a conductive solid electrolyte 3 of $Rb_4Cu_{16}I_7Cl_{13}$ which contains copper ions as electric charge carriers. An opposing electrode 13 which is made of mixture of the conductive solid electrolyte and copper is formed on an opposite surface of the conductive solid electrolyte 3 from the surface where the detecting electrode 2 is deposited. DC voltage which is supplied by a power source 17 is applied across the afore-mentioned supplying electrode 1 and the opposing electrode 13 through terminals 11a, 11b.

The operation of the above-mentioned conventional gas detector is as follows:

When copper layer which had been previously deposited on the detecting electrode 2 is electrolyzed with a constant current from the power source 17, that is, DC voltage is applied between the detecting electrode 2 as an anode and the opposing electrode 13 as a cathode, the metal copper in the detecting electrode 2 dissociates into copper ions [$Cu^+$] into the conductive solid electrolyte 3. The copper ions in the conductive solid electrolyte 3 move toward the opposing electrode 13 as a result of the application of the DC voltage. And copper is deposited on the opposing electrode 13 at the interface between the opposing electrode 13 and the conductive solid electrolyte 3.

In the above-mentioned electrolysis, a terminal voltage which is measured with a potentiometer 14 varies depending on time as shown in FIG. 5, which is a graph showing a terminal voltage-time relationship for the conventional gas detector. The terminal voltage between the terminals 11a, 11b is maintained at a constant voltage as far as the copper exists in the detecting electrode 2. The absence of the metal copper in the detecting electrode 2 renders the terminal voltage to rise suddenly as shown in FIG. 5, because of running out of the copper ions as electric charge carriers. The time interval from application of the terminal voltage to the terminals 11a, 11b to sudden rise of the terminal voltage is proportional to the quantity of metal copper which is deposited to the detecting electrode 2. The quantity of copper on the detecting electrode 2 is given by a subtraction of a quantity of copper [Cu] which is consumed by reacting with objective gas from an initial quantity of copper which originally existed as the detecting electrode 2.

FIG. 5 shows relationship between the time interval (abscissa) and the terminal voltage (ordinate) in the conventional gas detector. In FIG. 5, a curved line B indicates the relationship in a state when the metal copper on the detecting electrode 2 has not reacted to the objective gas yet, and a curved line A indicates the relationship in a state when the metal copper on the detecting electrode 2 has reacted to the objective gas. The time difference $\Delta t$ between the times of sudden rise of the voltage is detected as a value for indicating decomposed gas amount in the conventional gas detector. The reaction amount of the objective gas, that is of the composed $SF_6$ gas generated by electric discharging in the GIS can be measured with the conventional gas detector, and the conventional gas detector shows function as gas sensor for detecting electric discharging.

Since the above-mentioned conventional gas detector is small-sized and light-weight and able to measure the decomposed gas in the form of an electric signal, by providing it in a GIS an internal discharge of the GIS can be watched by using the conventional gas detector. However, the conventional gas detector has the following problems:

a. a special apparatus, for example a recorder is necessary for recording the measured data because the conventional gas detector does not have such function for recording the measured data by itself, and/or b. a power source for producing a constant current and a circuitry for measuring the time interval is necessary to be provided thereto, because the decomposed gas is detected by measurement of the time interval until a sudden rise of the terminal voltage at an application of a constant current. As a result, the conventional gas detector requires complicated peripheral equipment.

OBJECT AND SUMMARY OF THE INVENTION

An object of the present invention is to provide a gas detector which has a memory function for detected data, and which is able to continuously watch occurrence of the electric discharge in the gas-insulated substation (GIS) by a gas detector of an electric signal detecting type which is constructed in simple structure.

In order to achieve the above-mentioned object, the gas detector of the present invention comprises:

a detecting electrode, which has a surface to contact with objective gas to be detected and has a predetermined quantity of a metal element;

a first conductive solid electrolyte, one face whereof contacts with the detecting electrode, and which contains ions of the metal element;

a polarization electrode, which is provided on the other face of the first conductive solid electrolyte and does not transfer the ions of the metal element;

a second conductive solid electrolyte which is formed on the polarization electrode and contains ions of the metal element; and a reference electrode which is provided on the second conductive solid electrolyte.

The gas detector in accordance with the present invention can memorize the detected data as an electric potential. Therefore, an apparatus for recording the detected data, such as a recorder need not be provided for the gas detector.

Since gas detection result is converted to a potential and is memorized in the shape of potential, the gas detector of the present invention does not require a circuitry for measuring a time interval for applying a constant current of electric power.

And further, the gas detector of the present invention can continuously watch the occurrence of the electric discharging in the gas-insulated substation (GIS), and further can be easily installed in the GIS because of simple structure and small-sized bulk.

While the novel features of the invention are set forth particularly in the appended claims, the invention, both as to organization and content, will be better understood and appreciated, along with other objects and features thereof, from the following detailed description taken in conjunction with the drawings.

It will be recognized that some or all of the Figures are schematic representations for purposes of illustration and do not necessarily depict the actual relative sizes or locations of the elements shown.

DESCRIPTION OF THE PREFERRED EMBODIMENTS

Figure 1:
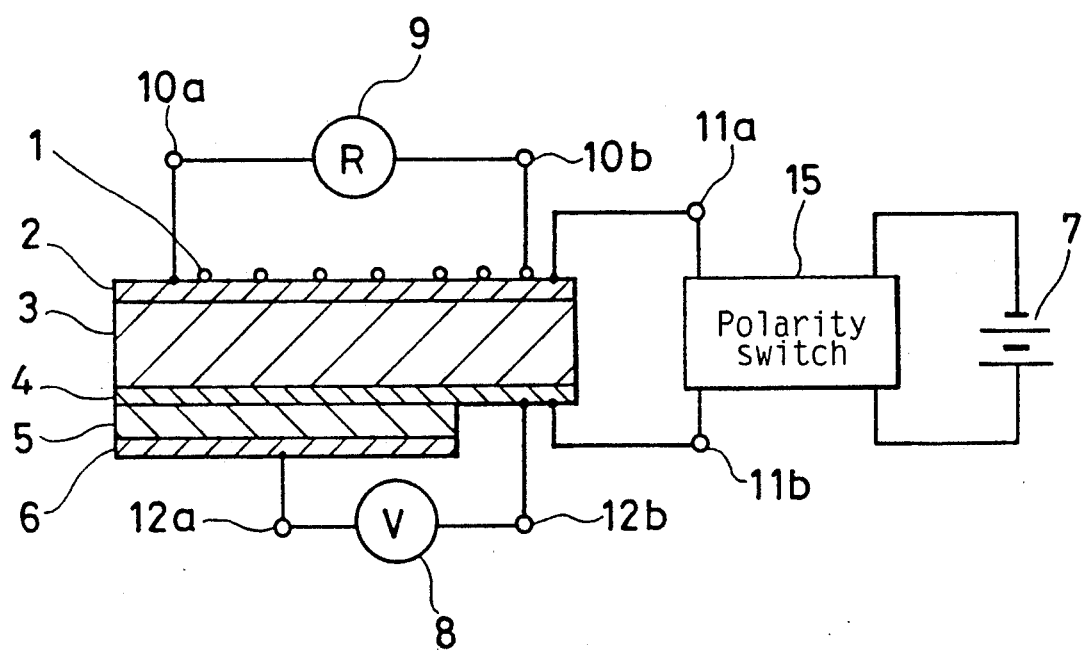
FIG. 1 is a sectional view with schematic circuit diagram showing a gas detector of a preferred embodiment of the present invention.
Figure 2:
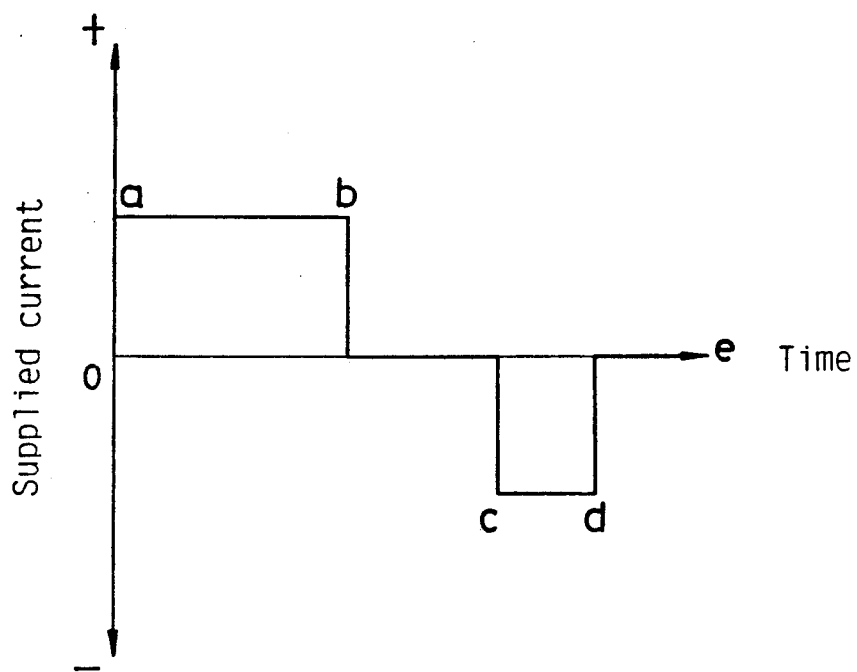
FIG. 2 is a graph showing a relationship of current vs. time of the gas detector shown in FIG. 1.
Figure 3:
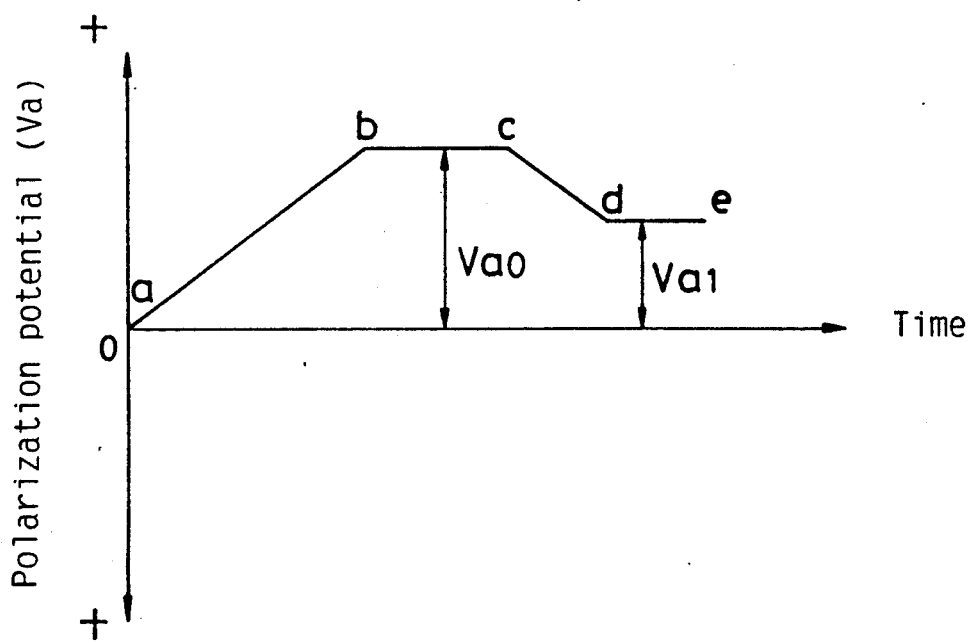
FIG. 3 is a graph showing a relationship of polarization potential vs. time of the gas detector shown in FIG. 1.
Figure 4:
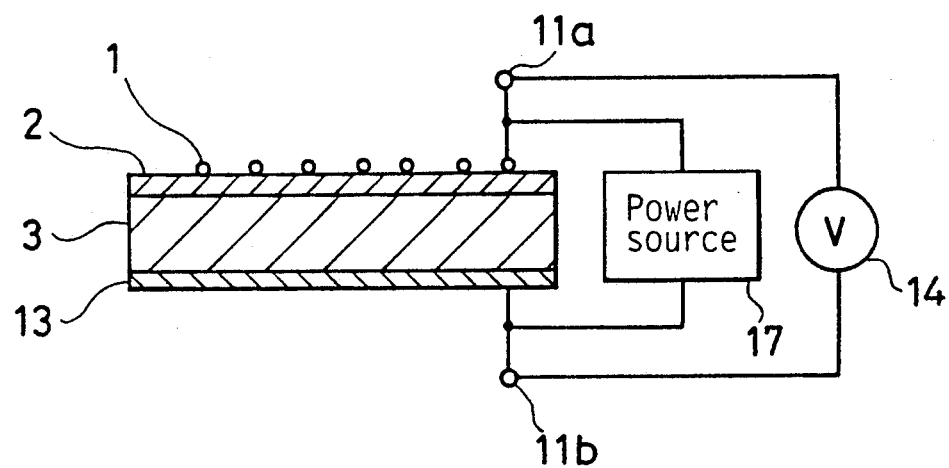
FIG. 4 is the sectional view with schematic circuit diagram showing the conventional gas detector.
Figure 5:
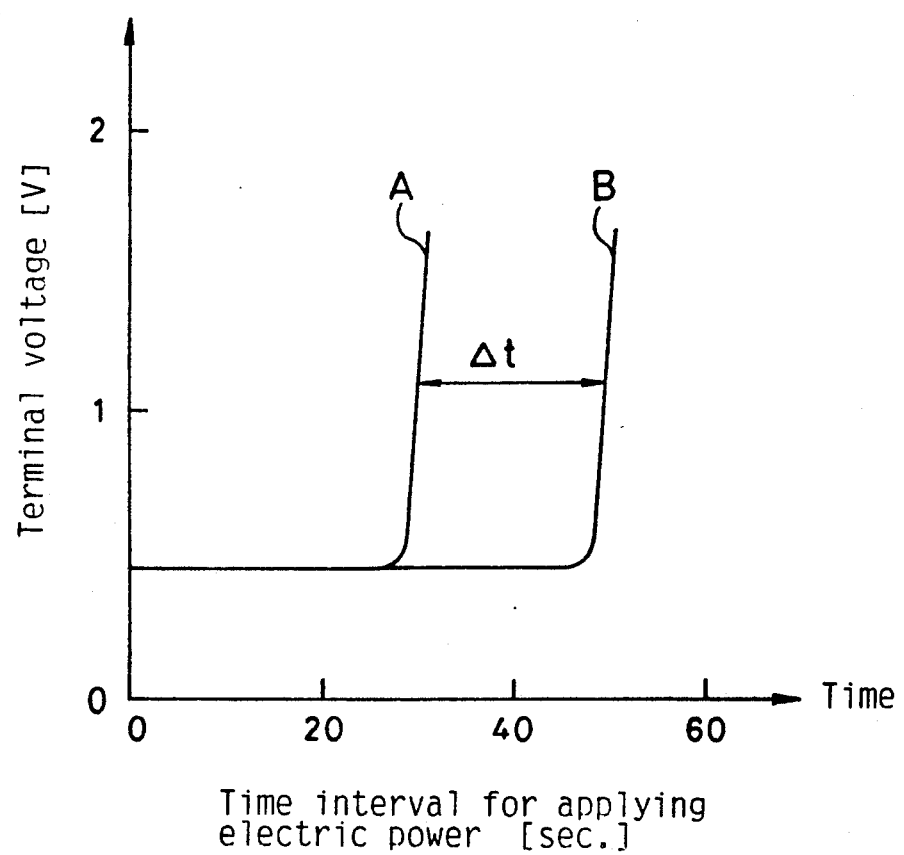
FIG. 5 is the graph showing the relationship of terminal voltage vs. time of the conventional gas detector shown in FIG. 4.

Hereafter, preferred embodiments of the present invention are elucidated with reference to the accompanying drawings of FIGS. 1 to 3.

FIG. 1 shows a sectional view with schematic circuit diagram of a gas detector in accordance with the present invention. In FIG. 1, a supplying electrode 1 which is made of platinum [Pt] wires formed in mesh shape is formed in an electrically conductive manner on a detecting electrode 2 for supplying electricity therethrough. The detecting electrode 2 is made of a deposition layer of silver [Ag], which is for reacting with the decomposed $SF_6$ gas, such as fluorine [$F_2$] gas. A first conductive solid electrolyte 3 which is formed to contact with a surface of the detecting electrode 2 is made of silver sulfide iodide [$Ag_3SI$]. A polarization electrode 4 which is made of silver selenide [$Ag_2Se$] is provided on a face of the first conductive solid electrolyte 3, which face is opposite to the face whereon the detecting electrode 2 is formed. A second conductive solid electrolyte 5 which is also made of silver sulfide iodide [$Ag_3SI$] is formed on the face of the polarization electrode 4. A reference electrode 6 which is made of silver is provided on the face of the second conductive solid electrolyte 5.

DC electric voltage is supplied by a power source 7 through a polarity switch 15 and terminals 11a and 11b to the supplying electrode 1 and the polarization electrode 4. The terminal 11a is connected to the supplying electrode 1, and the terminal 11b is connected to the polarization electrode 4. Polarity of DC electric voltage from the power source 7 can be reversed by the polarity switch 15. The electric potential between the polarization electrode 4 and the reference electrode 6 is detected by a polarization potentiometer 8, which is connected across terminal 12a connected to the reference electrode 6 and terminal 12b connected to the polarization electrode 4. The resistance between the supplying electrode 1 and the detecting electrode 2 is measured by a resistance meter 9, which is connected across terminals 10a, 10b which are provided on opposite end parts of the detecting electrode 2. The terminals 10a, 10b are provided for measuring the resistance. The terminals 11a, 11b are provided for supplying electric voltage. The terminals 12a, 12b are provided for measuring polarization potential.

Next, operation of the above-mentioned gas detector is described for the case of detection fluorine [$F_2$], which is one gas resulting from decomposition of $SF_6$.

In a first step, prior to exposition of the detecting electrode 2 to the objective gas to be detected, the detecting electrode 2 and the polarization electrode 4 are electrified by the power source 7 so that silver ions [$Ag^+$] in the first conductive solid electrolyte 3 flow toward the detecting electrode 2. As a result, silver is deposited on the detecting electrode 2 as shown by the following reaction formula:

$$Ag^+ + e^- \rightarrow Ag \qquad (1)$$

In other words, a predetermined quantity of metal ions in the first conductive solid electrolyte 3 is deposited on the detecting electrode 2, by means of electrification made by rendering the polarization electrode 4 as anode, and the detection electrode 2 as cathode.

In the above-mentioned circumstance, only a few silver ions are supplied from the polarization electrode 4 [$Ag_2Se$] to the first conductive solid electrolyte 3 [$Ag_3SI$], and accordingly the first conductive solid electrolyte 3 adjacent to the polarization electrode 4 has excess anions. Therefore, a positive charge which corresponds to the excess anions is induced on the polarization electrode 4. And, potential difference between the polarization electrode 4 and the reference electrode 6, namely polarization potential Va is generated. Electrification from the power source 7 across the detecting electrode 2 and the polarization electrode 4 is possible until the polarization potential Va reaches a decomposition potential of the conductive solid electrolyte. In case of using the silver sulfide iodide [$Ag_3SI$] as conductive solid electrolyte, the electrification is possible until the polarization potential Va reaches around 0.6 V. The decomposition potential is given as the minimum potential at which an electrochemical process can take place continuously at an appreciable rate.

The above-mentioned state where the DC voltage is applied to the detecting electrode 2 as cathode is shown by line a-b in FIG. 2 and FIG. 3. FIG. 2 shows the graph of a supplied current vs. time relationship between the detecting electrode 2 and the polarization electrode 4. FIG. 3 shows the graph of a polarization potential vs. time relationship between the polarization electrode 4 and the reference electrode 6. The polarization potential Va is directly proportional to quantity of metal which is deposited on the detecting electrode 2, that is, the quantity of metal in proportion to the quantity of electricity energized from the power source 7. Therefore, the quantity of metal deposited on the detecting electrode 2 corresponds to a polarization potential Vao shown in FIG. 3.

When the objective gas, namely fluorine gas, which is produced by electric discharging in $SF_6$ gas, touches the detecting electrode 2, some silver [Ag] in the detecting electrode 2 is converted to silver fluoride [AgF] through a reaction with fluorine gas which is produced in the decomposed $SF_6$ gas. The reaction formula is as follows:

$$F_2 + 2Ag \rightarrow 2AgF \qquad (2)$$

The metal silver is consumed by the above-mentioned reaction. The quantity of the metal silver in the detecting electrode 2 decreases by the reaction, and the amount of decrease is determined by the reaction quantity with the objective gas, namely fluorine [$F_2$] gas, to be detected. Therefore, the reaction quantity is in proportion to fluorine gas concentration.

After the detecting electrode 2 had been exposed to the decomposed $SF_6$ gas, the polarity of DC voltage applied from the power source 7 is reversed by the polarity switch 15. Therefore, the remaining metal silver which is not yet reacted in the detecting electrode 2 is ionized by application of a reverse-bias voltage between the detecting electrode 2 and the polarization electrode 4 through the first conductive solid electrolyte 3. As a result, the silver ions return to the first conductive solid electrolyte 3, and the polarization potential Va decreases corresponding to the quantity of the silver which returns to the first conductive solid electrolyte 3. The above-mentioned state is shown by line c-d in FIG. 2 and FIG. 3. The polarization potential Va at this state is $Va_1$ shown in FIG. 3. This polarization potential $Va_1$ remains essentially constant after stop of supplying electric power from the power source 7. The potential difference between Vao and $Va_1$ is proportional to the reaction quantity with the objective gas to be detected.

The time of a point c is shown in FIG. 2. That is, a start time when the reverse current begins to flow, can be set at desired time in the gas detector of the present invention. The time of the point c should be started when the objective gas is detected in the gas-insulated substation (GIS). The detection of the objective gas can be made by the resistance meter 9, which is connected between the terminals 10a and 10b in the detecting electrode 2. The objective gas can be detected by change of the resistance of the detecting electrode 2 with the resistance meter 9. According to experiments, the generation of the fluorine gas produces silver fluoride on the face or in the layer of the detecting electrode 2, and changes the resistance between the terminals 10a and 10b. At this time when the change in the resistance is detected, the reverse-bias voltage may be applied to the gas detector by means of a known automatic switching means in the polarity switch 15. And the gas detector starts measuring of the quantity of decomposed $SF_6$ gas.

Apart from the above-mentioned embodiment wherein silver in the form of metal and silver sulfur iodide [$Ag_3SI$] as the first conductive solid electrolyte 3 and the second conductive solid electrolyte 5 are used, a modified embodiment may be such that: the metal and ionic conductive solid electrolyte are in a manner as shown by the following table 1.

TABLE 1

| Metal | Ionic conductive solid electrolyte |
|---|---|
| Ag | $Ag_3Si$, $RbAg_4I_5$, $Ag_6I_4WO_4$, AgI |
| Cu | $Rb_4Cu_{16}I_7Cl_{13}$, $CuPb_3Br_7$ mixture of CuBr 94 mole % and $C_6H_{12}N_4CH_3Br$ 12.5 mole % mixture of CuBr 94 mole % and $C_6H_{12}N_2(CH_3Br)_2$ 6 mole %, etc. |
| Li | LiI, $Li_3N$, $0.6Li_4GeO_4$—$0.4Li_3VO_4$, etc. |
| Na | Na—$\beta''Al_2O_3$, NaSiCON, etc. |

Apart from the above-mentioned embodiment wherein the objective gas to be detected is fluorine [$F_2$] in the decomposed $SF_6$ gas, a modified embodiment may be such that the objective gas is chlorine [$Cl_2$], sulfur dioxide gas [$SO_2$], hydrogen sulfide [$H_2S$], or the like.

Although the present invention has been described in terms of the presently preferred embodiments, it is to be understood that such disclosure is not to be interpreted as limiting. Various alterations and modifications will no doubt become apparent to those skilled in the art after having read the above disclosure. Accordingly, it is intended that the appended claims be interpreted as covering all alterations and modifications as fall with in the true spirit and scope of the invention.

What is claimed is:

1. A gas detector comprising:
   a detecting electrode having a surface contacting an objective gas to be detected and having a predetermined quantity of a metal element which reacts with the objective gas;
   a first conductive solid electrolyte including one face which contacts said detecting electrode, and which contains ions of said metal element;
   a polarization electrode provided on a face of said first conductive solid electrolyte opposite said face which contacts said detecting electrode, and which does not transfer ions of said metal element;
   a second conductive solid electrolyte including one face which contacts said polarization electrode and which contains ions of said metal element; and
   a reference electrode which is provided on a face of said second conductive solid electrolyte opposite said face which contacts said polarization electrode.

2. A gas detector in accordance with claim 1, which further comprises:
   a power source for applying a voltage across said detecting electrode and said polarization electrode; and
   a polarization potentiometer connected across and for measuring a potential difference between said polarization electrode and said reference electrode, thereby detecting a quantity of the metal deposited on said detecting electrode.

3. A gas detector in accordance with claim 2, which further comprises:
   terminals which are provided on opposite ends of said detecting electrode for measuring a resistance of said detecting electrode to detect the existence of said objective gas.

4. A gas detector in accordance with claim 3, which further comprises:

a polarity switch for reversing the polarity of said power source when said resistance of said detecting electrode indicates said objective gas is present.

5. A gas detector comprising:

a detecting electrode having a surface which contacts an objective gas to be detected and having a predetermined quantity of a metal element which reacts with the objective gas;

a first conductive solid electrolyte including one face which contacts said detecting electrode, and which contains ions of said metal element;

a polarization electrode provided on a face of said first conductive solid electrolyte opposite said face which contacts said detecting electrode, and which does not transfer said ions of said metal element;

a second conductive solid electrolyte including one face which contacts said polarization electrode and which contains ions of said metal element;

a reference electrode which is provided on a face of said second conductive solid electrolyte opposite said face which contacts said polarization electrode;

a power source for applying a voltage across said detecting electrode and said polarization electrode;

terminals provided on opposite ends of said detecting electrode for detecting a resistance of said detecting electrode; and a polarity switch for automatically reversing the polarity of said voltage applied across said detecting and said polarization electrodes when a change in resistance of said detecting electrode is detected after said electrode is exposed to said objective gas.

6. A gas detector comprising:

a detecting electrode having a surface contacting an objective gas to be detected and having a predetermined quantity of a metal element;

a first conductive solid electrolyte including one face which contacts said detecting electrode and which contains ions of said metal element;

a polarization electrode provided on a face of said first conductive solid electrolyte opposite said face which contacts said detecting electrode, and which does not transfer ions of said metal element;

a second conductive solid electrolyte including one face which contacts said polarization electrode and which contains ions of said metal element;

a reference electrode which is provided on a face of said second conductive solid electrolyte opposite said face which contacts said polarization electrode;

a power source for applying a voltage across said detecting electrode and said polarization electrode;

a polarization potentiometer connected across and for measuring a potential difference between said polarization electrode and said reference electrode, thereby detecting a quantity of metal deposited on said detecting electrode; and terminals provided on opposite ends of said detecting electrode for measuring a resistance of said detecting electrode to detect the existence of said objective gas.

* * * * *